United States Patent [19]
Ellingboe

[11] Patent Number: 5,653,681
[45] Date of Patent: Aug. 5, 1997

[54] METHOD AND SYSTEM FOR OBTAINING TARGET INFUSION DOSAGE

[75] Inventor: Bruce S. Ellingboe, Littleton, Colo.

[73] Assignee: COBE Laboratories, Inc., Lakewood, Colo.

[21] Appl. No.: 475,019

[22] Filed: Jun. 6, 1995

[51] Int. Cl.$^6$ .......................... A61M 37/00; A61M 31/00
[52] U.S. Cl. .............................. 604/4; 604/49; 604/65; 128/DIG. 3
[58] Field of Search .................................. 604/4, 49, 82, 604/92, 93, 65, 27, 207, 246, 317, 318; 128/DIG. 3

[56] References Cited

U.S. PATENT DOCUMENTS

| | | |
|---|---|---|
| 5,230,341 | 7/1993 | Polaschegg . |
| 5,385,540 | 1/1995 | Abbott et al. . |
| 5,423,749 | 6/1995 | Merte et al. . |

OTHER PUBLICATIONS

Houerous, D. et al. (1992) Ann. Thorac. Surg. 54:809–16.
Fried, D.W. & Mohamed, H. (1993) Perfusion 8:401–407.

*Primary Examiner*—Michael Powell Buiz
*Assistant Examiner*—Ellen Tao
*Attorney, Agent, or Firm*—Bruce R. Winsor; Edna M. O'Connor

[57] ABSTRACT

A method and system are disclosed for more accurate administration of a composition being infused into a body fluid having formed elements. The improved accuracy is due to a correction factor that corrects for the relative impermeability of the formed elements to the infused composition. In one embodiment, the infusion system is a cardioplegia system in which a controller receives information pertaining to the hematocrit and initial blood potassium concentration and adjusts blood flow rate and crystalloid (KCl) solution flow rate so as to obtain the desired resulting potassium concentration in the cardioplegia. The invention further includes an infusion system that comprises a controller which uses an equation that relates the correction factor to an index of formed elements in the body fluid, such as the hematocrit. The equation is determined empirically from a series of experiments in which the resulting concentration of the substance infused into the body fluid is correlated to a formed element index of the body fluid, such as hematocrit.

49 Claims, 3 Drawing Sheets

METHOD AND SYSTEM FOR OBTAINING TARGET INFUSION DOSAGE

FIELD OF THE INVENTION

The subject invention pertains to the controlled infusion of a composition into a body fluid containing formed elements. More particularly, it pertains to the controlled infusion of cardioplegia solution into blood.

BACKGROUND OF THE INVENTION

During open heart surgery, a system for the extracorporeal circulation of fluids through a number of fluid circuits is required. This system is referred to as a perfusion control system or heart-lung machine. The fluid circuits of the system typically include a cardiopulmonary circuit, a cardioplegia circuit, a cardiotomy circuit and a ventricular vent circuit.

The cardiopulmonary circuit, which is designed to functionally replace or supplement the heart and lungs during heart surgery, comprises tubing, one or more pumps for blood circulation and an oxygenation device. Blood is received from a major vessel entering the heart (e.g., the vena cava) by a venous line. The venous line transports blood optionally to a reservoir, and then to an oxygenator. Oxygenated blood is transported back to the patient via the arterial line and enters the patient in a major vessel leaving the heart (e.g., aorta).

The cardioplegia circuit delivers cardioplegia to the heart. Cardioplegia discontinues the beating of the heart in a manner that will minimize damage to the myocardium and provides a motionless heart on which the surgeon can operate. Cardioplegia can also supply other ingredients to provide for myocardial protection. Cardioplegia may be the crystalloid solution alone or may also include oxygenated blood diverted from the arterial line. The crystalloid solution typically contains potassium chloride (KCl), sugars and magnesium. The potassium (K+) concentration in the cardioplegia is initially elevated (e.g., 25 mmol/l) during induction of arrest and reduced (8.5-9 mmol/l). during maintenance. Other cations such as magnesium (Mg++) can be used as heart arresting agents. It is preferred to include oxygenated blood in the cardioplegia so that the cardioplegia is buffered and can oxygenate the myocardium. Where cardioplegia includes arterial blood, the cardioplegia circuit comprises the oxygenated blood line containing blood diverted from the arterial blood line, the crystalloid solution bag and line, the cardioplegia delivery line (containing the mixture of blood and crystalloid solution) and one or more pumps. The crystalloid solution line and the oxygenated blood line may both be threaded through the same pump or through different pumps. The pumps can be peristaltic or other pumps known in the art. There is typically a device for controlling and recording the total volume of crystalloid solution and oxygenated blood that are combined to form the cardioplegia. The cardioplegia is delivered to the coronary arterial network or coronary sinus for distribution throughout the myocardium. The cardioplegia is then distributed through the circulatory system, or may occasionally be drawn out the chest cavity and discarded or directed via the cardiotomy line to the cardiopulmonary circuit, as discussed immediately below.

The cardiotomy circuit is used to withdraw or suction blood or blood mixed with other fluids from the opened heart or the chest cavity and deliver it to the cardiopulmonary circuit at a point upstream of the oxygenator.

The ventricular vent circuit functions to drain the left ventricle of blood that returns via the bronchial artery and pulmonary veins. The vent line collects blood from the left ventricle and delivers it to the cardiopulmonary circuit at a point upstream of the oxygenator.

Existing systems for extracorporeal circulation commonly have pumps, reservoir(s), an oxygenator and monitoring devices mounted on a console. The system can also include a controller that regulates pump speeds and receives information from patient monitoring devices. The controller may also cause the collected information to be displayed on a monitor. A description of perfusion control systems can be found in U.S. Ser. No. 08/304,725, filed Sep. 12, 1994, pending, which is incorporated herein in its entirety by reference.

The infusion of KCl or other arresting agents into the patient's blood is critical to induce and maintain arrest during surgery. It is generally considered desirable to avoid excessive dilution of the blood with crystalloid solution so as to maintain adequate oxygenation of tissues and minimize the need for heat exchange (Houerou, D. et al. (1992) Ann. Thorac. Surg. 54:809–16). Thus, the trend is to use crystalloid solutions of high concentration. It is also considered desirable to avoid an excessive dose of KCl as it can result in increased systemic K+ concentration and delayed resumption of heart function at the conclusion of surgery.

To obtain a desired K+ concentration in the cardioplegia, cardiologists select the crystalloid solution concentration and the flow rates of oxygenated blood and crystalloid solution. See, e.g., Fried, D. W. & Mohamed, H. (1993) Perfusion 8:401–407. U.S. Pat. No. 5,385,540 (1995) describes a cardioplegia pump system for controlling the ratio of blood and crystalloid solution that are mixed.

A prior art equation that has been used to predict the K+ concentration in the cardioplegia is:

$$\frac{Q_b * C_s + Q_k * C_k}{Q_b + Q_k} = C_o \qquad (1)$$

where $C_o$ is the desired K+ concentration in the cardioplegia, $Q_b$ is the flow rate of the oxygenated blood, $C_s$ is the initial K+ concentration in the oxygenated serum, $Q_k$ is the flow rate of crystalloid solution, and $C_k$ is the crystalloid K+ concentration. Equation (1) suffers from at least one major setback: it does not correct for the effect of the formed elements that are not substantially permeable to the infused cations, such as K+. Therefore, equation (1) consistently under-predicts the therapeutic K+ concentration.

Thus, in the prior art, practitioners believed the unfractionated cardioplegia K+ concentration to be the therapeutically effective dose. The subject invention recognizes that the actual therapeutic concentration is the cardioplegia plasma K+ concentration, which invariably is greater than the unfractionated cardioplegia K+ concentration. The subject invention remedies the prior art erroneous prediction method by recognizing the reduced volume in cardioplegia that is actually available for solubilizing K+. Further, the subject invention provides accurate methods for determining the actual volume in cardioplegia available for solubilizing K+ based on an empirical relationship between plasma volume and hematocrit.

SUMMARY OF THE INVENTION

The subject invention comprises a method for infusion of a composition into a body fluid having formed elements or cells. Because the method corrects for the presence of formed elements in the body fluid, it more accurately produces the desired composition concentration in the body fluid. The correction is necessary because the formed elements are not substantially permeable to the infused composition and the formed elements represent a significant fraction of the body fluid volume.

In one embodiment, the body fluid is whole blood, the formed elements are red blood cells, and the composition is K+ ion. The infusion system is a perfusion control system in which the K+ ion is infused into oxygenated blood in an extracorporeal circuit that returns the blood and cation mixture (cardioplegia) to the myocardium, where it arrests the beating of the heart.

In other embodiments, the body fluid can be white blood cell or platelet concentrates, and the substance can be any material that does not substantially permeate the formed elements.

As mentioned in the Background, the cation concentration in cardioplegia was incorrectly predicted in the prior art according to equation (1). This formula consistently calculates resultant cation concentrations in cardioplegia that are lower than measured cation concentrations because it fails to correct $Q_b$ for the formed element volume that is unavailable to the added K+. If $Q_s$ or the serum volume is used instead of $Q_b$, then a more accurate resultant cation concentration can be calculated.

As a practical matter, $Q_s$ cannot be easily measured in an infusion system because complete separation of serum from formed elements on-line is not feasible. Moreover, $Q_s$ cannot be accurately calculated solely from the hematocrit. Hematocrit, or the volume percent of red blood cells, is determined by sedimenting the red blood cells in whole blood by centrifugation. The conditions of centrifugation, such as radius length, rpm, g force and duration, determine the degree of separation of plasma from cells. Because the sedimented cells retain a residual layer of plasma around each cell and between cells, the hematocrit is always larger than the actual red cell volume. The red cell volume fraction is actually between 50% and 70% of the measured hematocrit, depending on the method of measuring hematocrit. Further, even for a given hematocrit measuring method, the actual red cell volume can vary as a function of the hematocrit value and the relationship between actual red cell volume and hematocrit value must be determined empirically. That is, the relationship between the red cell volume and the hematocrit value is not necessarily a constant proportion.

In accordance with the subject invention, a corrected formula for calculating the resulting concentration of cation in the cardioplegia is:

$$C_r = \frac{(Q_b/Z_i * C_s) + (Q_k * C_k)}{Q_b/Z_i + Q_k} \quad (2)$$

where $Z_i$ is the red cell volume correction factor at a given hematocrit, i, that converts $Q_b$ to $Q_s$. $Z_i=1/(1-RCVF)$ where RCVF is the fraction of the blood volume excluded by the red cell membranes. $Z_i$ can vary as a function of hematocrit; e.g., the higher the hematocrit, the greater the correction factor.

"Z" refers to the correction factor variable without regard to a specific hematocrit value. To obtain an equation relating Z to a range of hematocrit values, the following protocol can be used. A blood sample of known hematocrit and volume, $V_b$, is measured for the cation concentration, $D_s$ (e.g., using a Radiometer™ sodium/potassium analyzer having an ion selective electrode); then an aliquot ($V_k$) of cation solution of known concentration ($D_k$) is added to the blood sample, and the resulting concentration, $D_r$, is measured. This process is repeated several times with blood samples having the same hematocrit to yield several $Z_i$ values at the first hematocrit value. $Z_i$ is calculated from measurable concentration and volume data:

$$Z_i = \frac{V_b}{V_k} * \frac{D_r - D_s}{D_k - D_r} \quad (3)$$

Blood having a second hematocrit value is then tested in the same manner to obtain a second series of $Z_i$ values. The process can be repeated for multiple blood samples each having different known hematocrits. The collected $Z_i$ values are plotted against their respective hematocrit values and an equation relating Z to hematocrit is obtained from the plot.

Alternatively, an equation relating Z to hematocrit can be obtained by using an analogous protocol with blood and crystalloid flow rates rather than volumes. $Z_i$ is calculated from the measured concentration and flow rate data according to equation (3a):

$$Z_i = \frac{Q_b}{Q_k} * \frac{C_r - C_s}{C_k - C_r} \quad (3a)$$

where $Q_b$ is the blood flow rate, $Q_k$ is the crystalloid flow rate, $C_r$ is the resulting cardioplegia concentration, $C_k$ is the crystalloid solution concentration, and $C_s$ is the initial serum concentration of cation.

As is described hereinbelow in Example 1, the aforementioned protocol relating to equation (3) was used with bovine blood to empirically determine an equation relating Z to hematocrit. The following equation was derived:

$$Z = .906 * e^{.00995 * Hct} \quad (4)$$

The invention further comprises a method for correcting $C_r$ for the effect of differences in osmolarity between the crystalloid solution and the intracellular plasma. In whole blood, the osmolarity of the blood plasma is usually maintained at a slightly lower value than that of the intracellular plasma. When crystalloid solution is added to the blood, water flows out of the red blood cells. The blood plasma ion concentration is reduced by the additional water.

The foregoing equation (4) which was obtained by a least squares exponential fit to data obtained in Example 1 below, takes into account the differential osmolarity effect for a crystalloid solution of 400 mEq/l and an initial blood K+ concentration of approximately 5 mEq/l. However, when crystalloid solution concentration is higher than 400 mEq/l, it may be desirable to adjust formula (2) to further accommodate the greater differential osmolarity effect. The differential osmolarity effect at crystalloid concentrations over 400 mEq/l may result in a curve that deviates significantly from the exponential or linear curve observed for lower crystalloid concentrations. While it is possible to derive an equation that fits the curve over a range of crystalloid concentration from 0 to values in excess of 400 mEq/l, clinical application of the subject method does not require such a comprehensive equation. It could be sufficient at higher crystalloid concentrations to use both the Z correction factor derived for lower crystalloid concentrations and a volume correction factor that reflects the volume of water contributed by the red blood cells when using crystalloid solution having a concentration in excess of 400 mEq/l. The adjusted formula that includes the water contributed by red blood cells is:

$$C_r = \frac{(Q_b/Z_i * C_s) + (Q_k * C_k)}{Q_b/Z_i + Q_k + \Delta Q_{rc}} \quad (5)$$

where $\Delta Q_{rc}$ is the change in the red cell volume.

$$\Delta Q_{rc} = Q_{rci} * \left[ 1 - \frac{O_s}{O_r} \right] \quad (6)$$

where $Q_{rci}$ is the initial red cell intracellular plasma volume, which is about 0.667 of the total red cell volume, RCVF. As mentioned above, RCVF can be determined from the $Z_i$ for a particular hematocrit from $Z_i=1/(1-\text{RCVF})$. $O_s$ is the initial serum osmolarity, and $O_r$ is the resultant osmolarity of the blood after addition of the crystalloid solution.

Assuming that the osmolarity of the blood and intracellular serum are equal, the $O_r$ can be obtained by the following equation:

$$O_r = \frac{[(Q_{rci} + Q_b/Z_i) * O_s] + (Q_k * O_k)}{Q_{rci} + Q_b/Z_i + Q_k} \quad (7)$$

where $Q_{rci}$ is the initial red blood cell plasma volume (about 0.667 of the RCVF), $Q_b$ is the initial blood volume, $Z_i$ is the correction factor that converts $Q_b$ to $Q_s$ or initial serum volume, $O_s$ is the initial serum osmolarity (measured by a sodium/potassium analyzer), $Q_k$ is the volume of crystalloid added to the blood, and $O_k$ is the osmolarity of the crystalloid solution.

As the trend is to use crystalloid solutions of greater concentration so as to minimize blood dilution and attendant disadvantages, practitioners using such solutions can correct $C_r$ for $Q_{rc}$ per equation (5), rather than redetermining the relationship between Z and hematocrit for crystalloid solution concentrations in excess of 400 mEq/l.

Thus, the subject invention comprises an infusion method for obtaining a desired concentration of a composition in a body fluid having formed elements that are not substantially permeable by using an empirically determined equation relating a correction factor, Z, to the hematocrit or other measurable index of the formed elements. It further comprises an infusion system comprising a controller that receives information pertaining to the body fluid's initial composition concentration and hematocrit or formed element index, and controls one or more of the composition solution flow rate and concentration, and the body fluid flow rate to obtain a desired resulting composition concentration in the mixture of body fluid and composition. In particular, the infusion system can be a concentration, $C_r$, cardioplegia infusion system in which a controller receives $C_s$ and hematocrit information, and controls one or more of $C_k$, $Q_k$ and $Q_b$ to produce cardioplegia having a desired cation concentration, $C_r$.

More generally, the invention comprises a method for producing a mixture comprising a first fluid having a dissolved substance in a first concentration and blood having a volume of formed elements, where the formed elements are not substantially permeable to the dissolved substance, and the mixture has a predetermined concentration of the dissolved substance. The method comprises the steps of: establishing a volume of the blood; correcting the volume of the blood for the effects of the volume and permeability to the dissolved substance of the formed elements; establishing a volume of the first fluid to achieve the predetermined concentration of the dissolved substance in the mixture; and combining the volume of the first fluid with the volume of the blood to form the mixture. The correcting step involves determining the portion of the blood volume that comprises the formed elements. Because the formed elements respond to the presence of the dissolved substance in the mixture by transferring fluid from within the formed elements to a portion of the mixture outside the formed elements, the volume of the blood can further be adjusted for the effect of the transferred fluid.

The invention also generally comprises an apparatus for producing a mixture comprising a first fluid having a dissolved substance in a first concentration and blood having a volume of formed elements, with the formed elements being not substantially permeable to the dissolved substance, and the mixture having a predetermined concentration of the dissolved substance. The apparatus comprises: means for establishing a blood volume; means for correcting the blood volume for the effects of the volume and permeability to the dissolved substance of the formed elements; means for establishing a volume of the first fluid to achieve the predetermined concentration of the dissolved substance in the mixture; and means for combining the volume of the first fluid with the volume of the blood. The means for correcting the blood volume for the effects of volume and permeability of the formed elements can be a controller. The means for establishing the volume of the first fluid can be a first pump controlled by the controller. The means for establishing the blood volume can be a second pump controlled by the controller. The means for correcting the blood volume for the effects of volume and permeability of the formed elements can include a means for determining the ratio of the volume of formed elements to the total blood volume.

DETAILED DESCRIPTION OF THE INVENTION

A more complete understanding of the invention can be obtained from a description of the drawings which illustrate a heart-lung machine, the COBE Perfusion Control System™, sold by the assignee of the subject invention. As of the filing date of the subject application, the COBE Perfusion Control System has been sold without a control function and/or operator instructions that would effect the subject invention.

Figure 1:
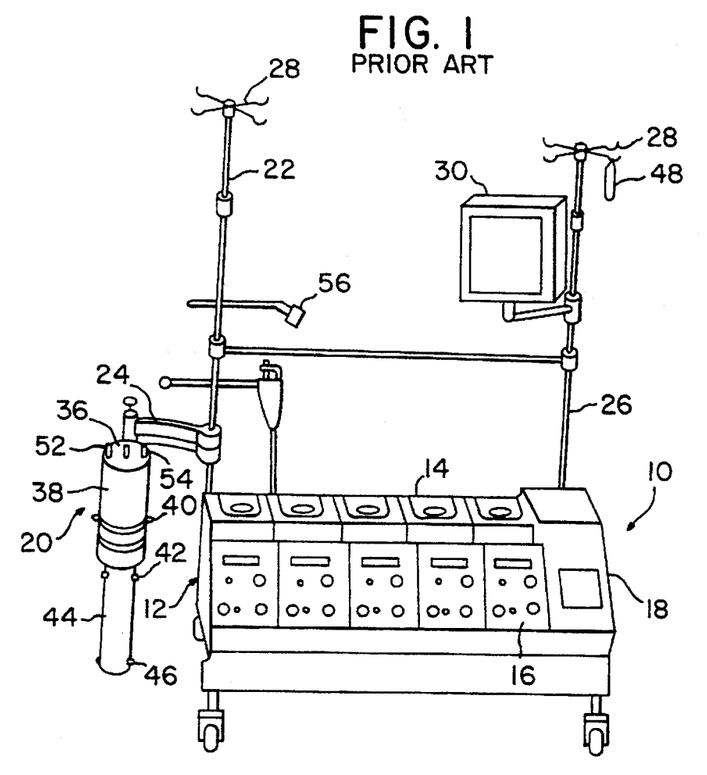
FIG. 1 is a pictorial representation of a perfusion control system.

FIG. 1 illustrates a horizontal row of six modules: five are pump assemblies 12 comprising peristaltic pump heads 14 and an instrument control panel 16; the sixth is a central control module 18. An assembly 20 of the oxygenator 44, heat exchanger and reservoir 38 ("oxygenator assembly") is mounted on a mast 22 with a swing arm 24. At the top of each of two masts 22, 26 are hooks 28 for hanging of crystalloid solution or other fluids. A display monitor 30 is mounted on mast 26, and is electronically connected to the central control unit 18. Pump assemblies 12 can be under the local control of their instrument panels 16 or may be under the control of the central controller 18. The central controller 18 can receive information from an arterial bubble sensor 56, a blood level sensor (not shown) in the reservoir 38, temperature sensors disposed in arterial or cardioplegia lines or in the patient (not shown), and pressure sensors disposed in the arterial, cardioplegia or left ventricle lines (not shown). The controller 18 processes such information and can communicate it to the monitor 30. The controller can respond to information by controlling the cardiopulmonary, cardioplegia and other pump heads 14. The central controller 18 and monitor 30 have keypads for perfusionist control of such functions or monitoring systems. The COBE Computerized Perfusion Controller Operator's Manual (May, 1990), incorporated herein in its entirety by reference, provides a complete description of the functions of the prior art central controller 18.

Figure 2:
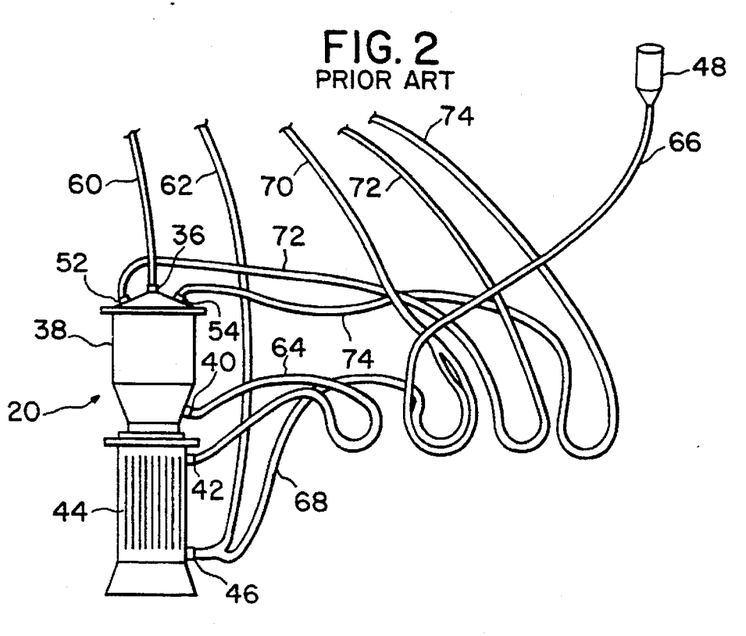
FIG. 2 is a schematic representation of the fluid circuits for the apparatus of FIG. 1.

FIG. 2 is a pictorial schematic illustrating only the prior art tubing and oxygenator assembly of FIG. 1. A venous line 60 which is connected to a major vessel entering the heart (not shown) transports blood from the patient to the venous port 36 of the reservoir 38. The cardiopulmonary pump loop 64 comprises a line connected to a second reservoir port 40 which is threaded through a peristaltic pump head 14 of a pump assembly 12 (FIG. 1), and which connects with a first oxygenator port 42 to transport blood from the reservoir 38 to the oxygenator 44. The arterial line 62, connected to a "Y" adaptor off a second oxygenator port 46, transports the oxygenated blood to a major vessel exiting the heart (not shown). The crystalloid solution supply line 66, connected to a crystalloid solution supply bag 48, together with the cardioplegia blood line 68, connected to the other stem of the "Y" adaptor off oxygenation port 46, are threaded through another peristaltic pump head 14 of a pump assembly 12 (FIG. 1), and then combined into one line to produce a cardioplegia delivery line 70, which transports the cardioplegia to the heart (not shown). Alternatively, the crystalloid solution supply line 66 and the cardioplegia blood line 68 can be threaded through different pump heads 14 of different pump assemblies 12. Additionally, a single pump assembly can contain a double pump head (not shown), such that lines 66 and 68 are threaded through separate pump heads located on the same pump assembly. Cardiotomy line 72, which is threaded through another peristaltic pump head 14 (FIG. 1), suctions blood and other fluids from the chest cavity (not shown) and transports it to a third reservoir port 52, whereby the fluid joins the cardiopulmonary circuit. Finally, a left ventricular vent line 74, which drains the left ventricle (not shown), is threaded through a fourth pump head 14 (FIG. 1), and transports blood to a fourth reservoir port 54, thereby relieving pressure in the ventricle.

Figure 3:
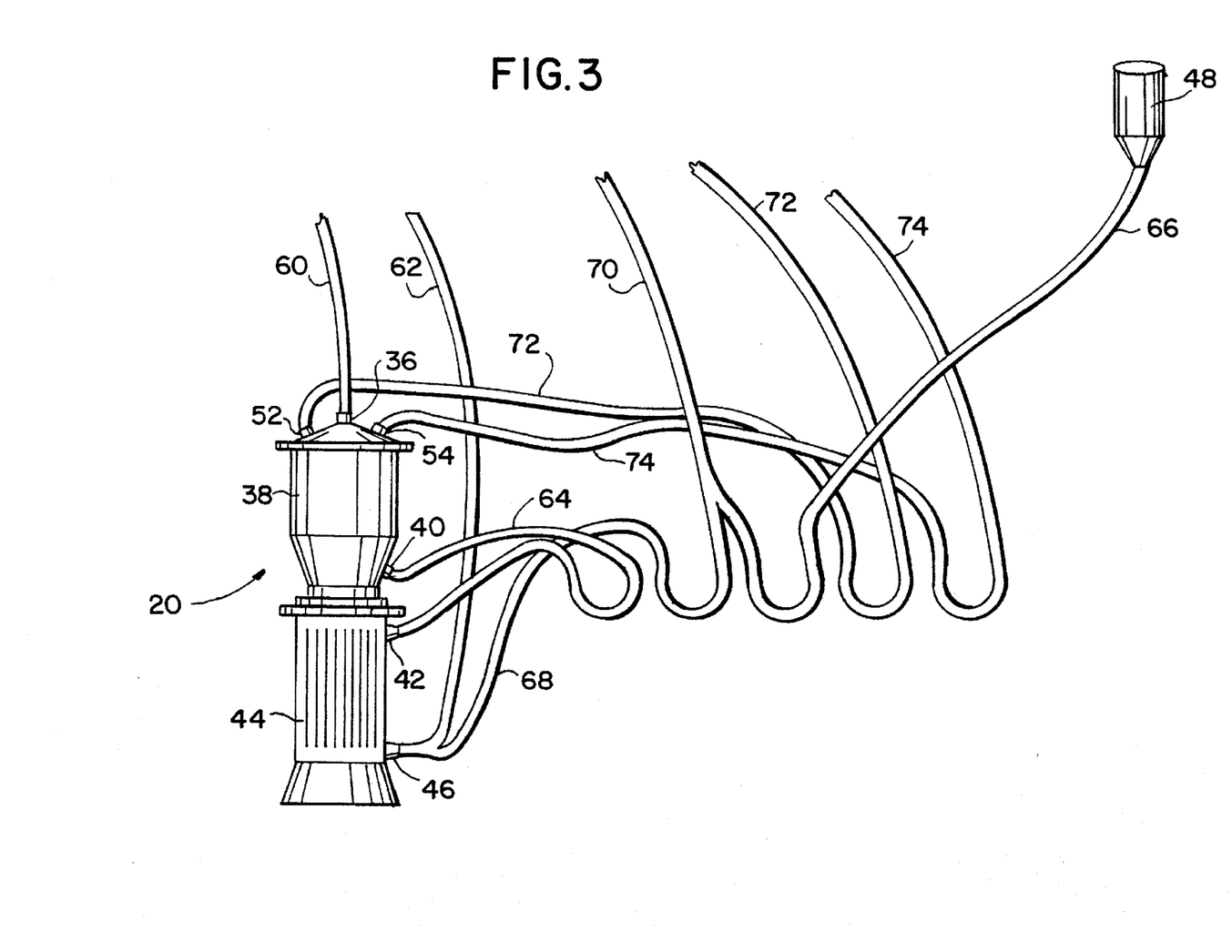
FIG. 3 is a schematic representation of the fluid circuits used in a preferred embodiment of the subject invention.

In the subject invention, the flow through lines 66 and 68 is regulated by selecting tubing diameters and/or selecting pump speeds. In a preferred embodiment, the lines are threaded through different pump heads (either on different pump assemblies or on a single pump assembly having a double pump head), and flow rate through each is independently regulated by independently controlled pump heads. Alternatively, the lines are threaded through the same pump head, but have diameters selected to produce a predetermined flow rate for a preselected pump speed. Thus, in either embodiment, the flow rates in the crystalloid supply line and the oxygenated blood line are independently controlled such that a desired $C_r$ is obtained. FIG. 3 illustrates the preferred embodiment in which the crystalloid supply line 66 and the cardioplegia blood line 68 are threaded through independent pump heads 14 (FIG. 1).

Figure 4:
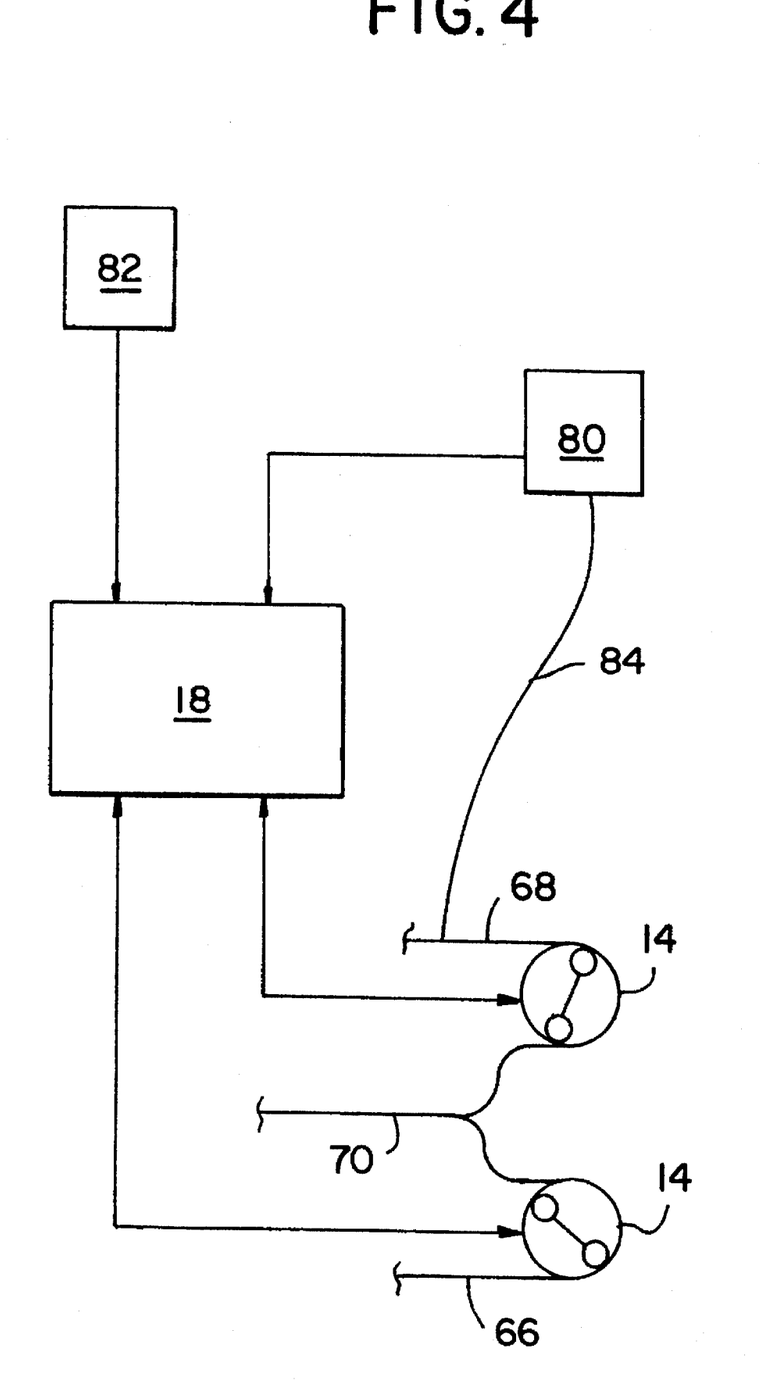
FIG. 4 is a schematic representation of a control system for the subject invention.

FIG. 4 illustrates a control system for the subject invention. The controller 18 receives information from an operator 82 and may also receive information from a hematocrit monitor 80. The hematocrit monitor 80 measures the patient's hematocrit in the cardioplegia blood line 68 or at a point upstream (e.g., in the reservoir 38 (FIG. 1)) via a fiber optic cable 84. In one embodiment, the monitor 80 is the COBE Saturation Hematocrit Monitor sold by the assignee of the subject application and described in U.S. Pat. No. 5,356,593, issued Oct. 18, 1994, incorporated herein in its entirety by reference. Other hematocrit monitors known in the art can be used. The hematocrit monitor 80 can supply hematocrit values to the controller 18 once or on a periodic or continuous basis. Alternatively, patient hematocrit can be determined by a hematocrit monitor 80 or other means and supplied to the controller 18 via the operator 82.

The operator 82 can also supply other information such as the initial patient serum K+ concentration ($C_s$) or blood flow rate ($Q_b$), the desired resulting cardioplegia concentration ($C_r$) or flow rate ($Q_r$), the crystalloid solution concentration ($C_k$) or flow rate ($Q_k$), to the controller 18. The controller calculates $Z_i$ from the hematocrit and the empirically derived equation relating Z to hematocrit. Using $Z_i$ and the information supplied by the operator, the controller can calculate the $Q_b$:$Q_k$ ratio, or $Q_b$, $Q_k$ or $C_k$ values that will produce the desired $C_r$. These variables are calculated using equations (2) and (3a). Thus, depending on the information supplied to the controller 18, it can calculate other variables of equations (2) and (3a). For example, the controller can calculate the $Q_b$:$Q_k$ ratio from $C_s$, $C_r$ and $C_k$, and then regulate pump heads 14 or specify diameters for the cardioplegia blood line 68 and the crystalloid solution line 66 to produce the desired $Q_b$:$Q_k$ ratio and $C_r$ in cardioplegia line 70. Additionally, the controller 18 could calculate the $C_k$ if it is supplied with $C_s$, $C_r$, $Q_b$ and $Q_k$. Also, the controller 18 can calculate $Q_k$ if it is supplied with $C_s$, $C_r$, $C_k$ and $Q_b$. Further, the controller 18 can calculate $Q_b$ if it is supplied with $C_s$, $C_r$, $C_k$ and $Q_k$. These and other calculations that can be performed by the controller 18 using equations (2) and (3a) will be readily apparent to those of skill in the art.

For example, once the $Q_b$:$Q_k$ ratio is calculated according to a rearranged equation (2), i.e., $$\frac{Q_b}{Q_k} = Z_i * \frac{C_k - C_r}{C_r - C_s} \qquad (2a)$$

the crystalloid solution flow rate, $Q_k$, can be determined by selecting a desired infusion mixture flow rate, $Q_r$, and calculating the $Q_k$ according to the equation:

$$Q_k = \frac{Q_r}{1 + Q_b/Q_k} \qquad (8)$$

Additionally, once the $Q_b$:$Q_k$ ratio is calculated according to equation (2a), the body fluid flow rate, $Q_b$, can be determined by selecting a desired infusion mixture flow rate, $Q_r$, and calculating the $Q_b$ according to the equation:

$$Q_k = \frac{Q_r * Q_b/Q_k}{1 + Q_b/Q_k} \qquad (9)$$

Further, once the $Q_b$:$Q_k$ ratio is calculated according to equation (2a), the crystalloid solution concentration, $C_k$, can be determined according to the equation:

$$C_k = C_r + \frac{Q_b}{Q_k} * \frac{(C_r - C_s)}{Z_i} . \qquad (10)$$

The subject invention is further detailed by reference to the following Examples. These Examples are provided for the purpose of illustrating the invention and are not intended to be limiting thereof.

EXAMPLE 1

Determination of Z, the Hematocrit Correction Factor

Bovine blood of a known hematocrit of 42 was treated with beef lung heparin. The blood was diluted with sterile normal saline solution (0.9% NaCl) to produce samples having hematocrit values of 40, 30 and 20. Aliquots of 200 mls of the blood samples were dispensed in beakers, such that there were three beakers of 40 hematocrit, two beakers of 30 hematocrit, and two beakers of 20 hematocrit blood. In Table 1, beakers 1–3 contain blood having hematocrit equal to 40; beakers 4–5 have hematocrits equal to 30 and beakers 6–7 have hematocrits equal to 20. Two hundred mls of saline was dispensed in beaker 8 as a control. K+ concentration was measured for each sample using a sodium/potassium analyzer. Tare and loaded weight were measured for each beaker.

About 1–3 mls of stock KCl solution (about 400 mEq/l) were added to each beaker, except beaker no. 1, which also served as a control. After KCl addition, the blood mixture was stirred and the K+ concentrations and weights were measured.

A second dose of KCl was added to each beaker (except beaker no. 1), and K+ concentrations and weights were measured. A total of 5 KCl aliquots were added to beakers 2–8, and weight and ion measurements were taken each time.

From the tare, initial and subsequent beaker weights, the blood mixture (cardioplegia) weights were calculated. Using density values (p, rho), the total blood or cardioplegia volumes were calculated. The density of the cardioplegia was determined by adding the densities of the component parts, i.e., of the red blood cells (1.098 g/ml), plasma (1.024 g/ml), and saline diluent (1.0046 g/ml):
(Hct=40)=1.098*0.4+1.024*0.6=1.0536
(Hct=30)=1.0098*0.3+1.024*0.45+1.0046*0.25=1.041
(Hct=20)=1.0098*0.2+1.024*0.3+1.0046*0.5=1.029

Table 1 presents the densities of blood and blood mixtures, the blood or blood mixture volume ($V_b$), the crystalloid solution volume ($V_k$), the initial concentration of potassium in the blood or mixture ($D_s$ or $D_r$), the resultant concentration of potassium after the aliquot of KCl is added ($D_r$), and the crystalloid concentration ($D_k$). The correction factor, $Z_i$, was calculated as according to equation (3). The $Z_i$ values were plotted against the hematocrit values and a least square exponential fit of the data yielded:

$$Z = 0.906427 e^{0.0099497 * Hct} \qquad (4)$$

TABLE 1

|  | Beaker 1 | Beaker 2 | Beaker 3 | Beaker 4 | Beaker 5 | Beaker 6 | Beaker 7 | Beaker 8 |
|---|---|---|---|---|---|---|---|---|
| *Initial* | | | | | | | | |
| Tare | 199.8 | 214.9 | 216.3 | 222.7 | 215.2 | 216 | 217.5 | 187.7 |
| Hct | 40 | 40 | 40 | 30 | 30 | 20 | 20 | 0 |
| Density | 1.05 | 1.05 | 1.05 | 1.04 | 1.04 | 1.03 | 1.03 | 1.0046 |
| $V_b$ | 190.2857 | 204.6667 | 206 | 214.1346 | 206.9231 | 209.7087 | 211.165 | 186.8405 |
| $D_s$ | 5.3 | 5.35 | 5.4 | 3.6 | 3.6 | 2.2 | 2.2 | 0 |
| *After 0.94 ml ($V_k$) of 397.34 mEq/l KCl ($D_k$)* | | | | | | | | |
| Hct | 40 | 40 | 40 | 30 | 30 | 19.5 | 19.5 | 0 |
| $D_r$ | 5.4 | 7.85 | 7.85 | 5.7 | 5.8 | 4.2 | 4.15 | 2 |
| $V_b$ | 190.2857 | 205.6067 | 206.94 | 215.0746 | 207.8631 | 210.6487 | 212.105 | 187.7805 |
| $Z_i$ |  | 1.397536 | 1.378508 | 1.221494 | 1.23688 | 1.134936 | 1.114106 | 1.005547 |
| *After 1.88 ml ($V_k$) of 397.34 mEq/l KCl ($D_k$)* | | | | | | | | |
| Hct | 40 | 39.5 | 39 | 29 | 29 | 19.5 | 19.5 | 0 |
| $D_r$ | 5.4 | 12.75 | 12.65 | 9.8 | 10.1 | 8.05 | 8 | 5.7 |
| $V_b$ | 190.2857 | 207.4867 | 208.82 | 216.9546 | 209.7431 | 212.5287 | 213.985 | 189.6605 |
| $Z_i$ |  | 1.375875 | 1.356537 | 1.197645 | 1.21426 | 1.097273 | 1.104718 | 0.934811 |
| *After 1.88 ml ($V_k$) of 397.34 mEq/l KCl ($D_k$)* | | | | | | | | |
| Hct | 40 | 39 | 39 | 28.5 | 29 | 19 | 18.5 | 0 |
| $D_r$ | 5.5 | 17.55 | 17.3 | 13.95 | 14.35 | 11.8 | 11.8 | 9.35 |
| $V_b$ | 190.2857 | 209.3667 | 210.7 | 218.8346 | 211.6231 | 214.4087 | 215.865 | 191.5405 |
| $Z_i$ |  | 1.377449 | 1.34263 | 1.235784 | 1.224443 | 1.088975 | 1.110913 | 0.94021 |
| *After 2.82 ml ($V_k$) of 397.34 mEq/l KCl ($D_k$)* | | | | | | | | |
| Hct | 40 | 38 | 38 | 28 | 28 | 19 | 19 | 0 |
| $D_r$ | 5.55 | 24.1 | 24 | 19.9 | 20.45 | 17.4 | 17.35 | 14.8 |
| $V_b$ | 190.2857 | 212.1867 | 213.52 | 221.6546 | 214.4431 | 217.2287 | 218.685 | 194.3605 |
| $Z_i$ |  | 1.280431 | 1.317228 | 1.204323 | 1.195243 | 1.104363 | 1.101937 | 0.954086 |
| *After 2.82 ml ($V_k$) of 397.34 mEq/l KCl ($D_k$)* | | | | | | | | |
| Hct | 40 | 37 | 37 | 27 | 27 | 18 | 18.5 | 0 |
| $D_r$ | 5.6 | 30.45 | 30.4 | 25.6 | 26.25 | 22.7 | 22.65 | 20.1 |
| $V_b$ | 190.2857 | 215.0067 | 216.34 | 224.4746 | 217.2631 | 220.0487 | 221.505 | 197.1805 |
| $Z_i$ |  | 1.280131 | 1.297971 | 1.187011 | 1.170244 | 1.074556 | 1.081617 | 0.9549 |

EXAMPLE 2

Illustration of the Effect of the Correction Factor on Resulting Concentration Determinations of corrected $C_r$ and uncorrected $C_r$ ($C_0$) were performed for a hypothetical cardioplegia system having a blood supply line and a crystalloid solution supply line combining their respective volumes in a ratio of $Q_b:Q_k=4:1$. The $C_s$ was assumed to be 5 mEq/l and the hematocrit of the blood samples was assumed to range from 15 to 35%. The $C_k$ was set at 30 mEq/l for maintenance of the arrested state and 100 mEq/l for induction of the arrested state.

For blood samples having hematocrit values of 15, 16, 17 35, $C_r$ was calculated using equation (2):

$$C_r = \frac{(Q_b/Z_i * C_s) + (Q_k * C_k)}{Q_b/Z_i + Q_k} \qquad (2)$$

where $Z_i = 0.906427 * e^{0.00995 * Hct}$.

$C_0$, the resultant concentration that would have been obtained without a hematocrit correction factor, was also calculated by using the prior art equation (1):

$$C_0 = \frac{Q_b * C_s + Q_k * C_k}{Q_b + Q_k} \quad (1)$$

The $E_i$ or error, $C_r-C_0$, is set forth below.

|     | Maintenance $C_k$ | | Induction $C_k$ | |
| --- | --- | --- | --- | --- |
| Hct | $C_r$ | $E_i$ | $C_r$ | $E_i$ |
| 15 | 10.21 | 0.21 | 24.799 | 0.799 |
| 16 | 10.252 | 0.252 | 24.956 | 0.956 |
| 17 | 10.293 | 0.293 | 25.114 | 1.114 |
| 18 | 10.335 | 0.335 | 25.273 | 1.273 |
| 19 | 10.377 | 0.377 | 25.433 | 1.433 |
| 20 | 10.419 | 0.419 | 25.594 | 1.594 |
| 21 | 10.462 | 0.462 | 25.756 | 1.756 |
| 22 | 10.505 | 0.505 | 25.918 | 1.918 |
| 23 | 10.548 | 0.548 | 26.082 | 2.082 |
| 24 | 10.591 | 0.591 | 26.246 | 2.246 |
| 25 | 10.635 | 0.635 | 26.412 | 2.412 |
| 26 | 10.678 | 0.678 | 26.578 | 2.578 |
| 27 | 10.722 | 0.722 | 26.745 | 2.745 |
| 28 | 10.767 | 0.767 | 26.914 | 2.914 |
| 29 | 10.811 | 0.811 | 27.083 | 3.083 |
| 30 | 10.856 | 0.856 | 27.253 | 3.253 |
| 31 | 10.901 | 0.901 | 27.423 | 3.423 |
| 32 | 10.946 | 0.946 | 27.595 | 3.595 |
| 33 | 10.992 | 0.992 | 27.768 | 3.768 |
| 34 | 11.037 | 1.037 | 27.941 | 3.941 |
| 35 | 11.083 | 1.083 | 28.116 | 4.116 |

These data indicate that the error increases with increasing hematocrit value and with increased crystalloid concentrations.

EXAMPLE 3

Illustration of the Effect of the Correction Factor on Resulting Concentration Determinations of corrected $C_r$ and uncorrected $C_r$ ($C_0$) were performed for a hypothetical cardioplegia system having a higher crystalloid concentration of 400 mEq/l. Higher concentrations are generally preferred to reduce blood dilution. The resulting cardioplegia flow, $Q_r$, was assumed to be 100 ml/min and $C_s$ was assumed to be 5 mEq/l. $Q_b$ and $Q_k$ values that would accommodate the high $C_r$ were calculated. However, the $Q_b$ and $Q_k$ values were not corrected for hematocrit so that the error that is generated by prior art methods could be assessed. The $Q_b$ and $Q_k$ values were calculated using the following equations, assuming that the $C_r$=10 mEq/l during maintenance and $C_r$=25 mEq/l during induction, and Hct=0:

$$Q_b = Q_r * \frac{C_k - C_r}{C_k - C_s} \quad (11)$$

and $$Q_k = Q_r - Q_b . \quad (12)$$

Equation (11) was derived as follows. Given that $Q_k+Q_b=Q_r$, $Q_b$ can be expressed in terms of the $Q_b$:$Q_k$ ratio as:

$$Q_b = \frac{Q_r * (Q_b/Q_k)}{1 + Q_b/Q_k} \quad (13)$$

Equation (3a) can be rearranged to:

$$\frac{Q_b}{Q_k} = Z_i * \frac{C_k - C_r}{C_r - C_s} .$$

Since no correction is made for hematocrit, Hct=0 and $Z_i$=1, resulting in the $Z_i$ term being dropped out of the rearranged (3a) equation. If the $Q_b/Q_k$ equation (3a) is then substituted into equation (13), equation (11) is obtained.

Equation (12) is a rearrangement of $Q_k+Q_b=Q_r$. The calculated $Q_b$ and $Q_k$ values at maintenance and induction crystalloid and blood flow rates were:

|     | Maintenance | Induction |
| --- | --- | --- |
| $Q_b$ | 98.734 | 95.19 |
| $Q_k$ | 1.266 | 4.81 |

Using these uncorrected $Q_b$ and $Q_k$ values, the actual $C_r$ values corrected for a range of hematocrit values (15 to 35), were calculated according to equation (2):

$$C_r = \frac{(Q_b/Z_i * C_s) + (Q_k * C_k)}{Q_b/Z_i + Q_k}$$

where $Z_i = 0.906427 * e^{0.00995 * Hct}$.

Additionally, corresponding $C_0$ values which did not reflect corrections for hematocrit, were calculated using equation (1):

$$C_0 = \frac{Q_b * C_s + Q_k * C_k}{Q_b + Q_k}$$

The $E_i$ or error, $C_r-C_0$, is set forth below.

|     | Maintenance $C_k$ | | Induction $C_k$ | |
| --- | --- | --- | --- | --- |
| Hct | $C_r$ | $E_i$ | $C_r$ | $E_i$ |
| 15 | 10.262 | 0.262 | 24.958 | 0.958 |
| 16 | 10.314 | 0.314 | 25.149 | 1.149 |
| 17 | 10.367 | 0.367 | 25.341 | 1.341 |
| 18 | 10.42 | 0.42 | 25.534 | 1.534 |
| 19 | 10.474 | 0.474 | 25.73 | 1.73 |
| 20 | 10.528 | 0.528 | 25.927 | 1.927 |
| 21 | 10.583 | 0.583 | 26.126 | 2.126 |
| 22 | 10.638 | 0.638 | 26.327 | 2.327 |
| 23 | 10.694 | 0.694 | 26.53 | 2.53 |
| 24 | 10.75 | 0.75 | 26.734 | 2.734 |
| 25 | 10.807 | 0.807 | 26.941 | 2.941 |
| 26 | 10.865 | 0.865 | 27.149 | 3.149 |
| 27 | 10.923 | 0.923 | 27.359 | 3.359 |
| 28 | 10.982 | 0.982 | 27.571 | 3.571 |
| 29 | 11.041 | 1.041 | 27.784 | 3.784 |
| 30 | 11.1 | 1.1 | 28. | 4. |
| 31 | 11.161 | 1.161 | 28.218 | 4.218 |
| 32 | 11.222 | 1.222 | 28.437 | 4.437 |
| 33 | 11.283 | 1.283 | 28.659 | 4.659 |
| 34 | 11.345 | 1.345 | 28.882 | 4.882 |
| 35 | 11.408 | 1.408 | 29.107 | 5.107 |

As with Example 2, these data indicate that the error increases with increasing hematocrit value and with increasing crystalloid concentration.

EXAMPLE 4

Clinical Study

A prototype cardioplegia administration system designed for variable potassium concentration control and more accurate $C_r$ calculation was employed in a clinical study conducted at St. Paul's Hospital in Vancouver, Canada. There were 30 patients in the study.

Thirteen were treated according to St. Paul's standard procedure (a prior art procedure without hematocrit correction) which employed a 4:1 $Q_b:Q_k$ ratio, and which used an induction $C_k$ of 100 mEq/l, a maintenance $C_k$ of 30 mEq/l and a desired $C_r$ of 24 mEq/l at induction or 10 mEq/l at maintenance ("Standard Group").

Seventeen were treated using a variable potassium dosage protocol which employed a single $C_k$ of 400 mEq/l ("Variable Group"). The variable potassium dosage prototype apparatus consists of two peristaltic pumps with a control/display panel; one pump meters the crystalloid solution and the second pump meters the oxygenated blood into the cardioplegia line. The prototype contains software that calculates the $Q_b:Q_k$ ratio necessary to obtain the desired $C_r$, and regulates the crystalloid solution pump and the oxygenated blood pump accordingly. The patient $C_s$ and hematocrit were measured after the institution of bypass, but before the cardioplegic arrest, and the $C_s$ and $C_k$ values were input into the prototype software. The software, using equation (2) and an assumed patient hematocrit i=25, calculates the $Q_b:Q_k$ ratio necessary to obtain the desired $C_r$. After the desired $Q_r$ is input into the software, the $Q_b$ and $Q_k$ can be calculated from the $Q_b:Q_k$ ratio. In the variable potassium protocol, the $C_r$ was initially set at 25 mEq/l with $Q_r$=300 ml/min, and $C_r$ was decreased in increments of 3 mEq/l to 8 or 10 mEq/l. If cardiac activity resumed during the stepwise decrease in $C_r$, the crystalloid concentration was increased to 15 mEq/l until activity stopped, and then incrementally decreased to 8–13 mEq/l. Once the lowest, steady state, heart-inactivating $C_r$ was achieved, cardioplegia hematocrit and cardioplegia potassium concentration were measured at intervals of about 3 minutes ($T_1$), 33 minutes ($T_2$) and 63 minutes ($T_3$).

Table 2 presents general information about the patients in the Standard and Variable Groups. Table 3 presents $C_r$ measured at established times $T_1$, $T_2$ and $T_3$ after initiation of crystalloid infusion minus the predicted cardioplegia K+ concentration.

TABLE 2

| Parameter | Standard Gp Avr | Variable Gp Avr |
|---|---|---|
| Age (yrs) | 58.1 | 63.8 |
| Sex | 2 f, 11 m | 7 f, 10 m |
| Weight (kg) | 79.7 | 79.7 |
| Pre-Op systemic K+ | 3.97 | 3.92 |
| Operative initial systemic K+ (mEq/l) | 4.5 | 4.2 |
| Operative systemic Hct (%) | 23.4 | 25.1 |
| Total K+ dose (mEq) | 73 | 61 |
| Operative Avr Systemic K+ (mEq/l) | 6.1 | 5.3 |
| Cardioplegia Hct (%) | 19.5 | 24.5 |
| Crystalloid Vol (ml) | 1700 | 152 |
| Total Cardioplegia Volume (ml)[1] | 8500 | 6510 |
| Cardioplegia $O_2$ cap/min (cc $O_2$/min)[1] | 6.4 | 9.6 |

[1]Assumes 100% cardioplegia blood oxygen saturation.

TABLE 3

| | Measured minus target $C_r$ | | | Average | Average |
|---|---|---|---|---|---|
| Pat Id | $T_1$ | $T_2$ | $T_3$ | $T_2$ & $T_3$[2] | $T_1$, $T_2$, $T_3$ |
| STANDARD GROUP | | | | | |
| 3 | 7.8 | 4.3 | NA | 4.3 | 6.1 |
| 6 | −3.6 | 1 | 1.1 | 1.1 | −0.5 |
| 9 | −2.5 | 4.2 | 1.8 | 3.0 | 1.2 |
| 12 | 9.8 | 4 | NA | 4.0 | 6.9 |
| 14 | 9.8 | 2 | NA | 2.0 | 5.9 |
| 15 | 13.1 | 2.7 | NA | 2.7 | 7.9 |
| 17 | −1.7 | 3.2 | 0.3 | 1.8 | 0.6 |
| 18 | 7.6 | 2.3 | 1.6 | 2.0 | 3.8 |
| 19 | 7.7 | 9.9 | −0.1 | 4.9 | 5.8 |
| 21 | 3.1 | 0.4 | NA | 0.4 | 1.8 |
| 23 | −1 | 0.3 | 0.6 | 0.5 | 0.0 |
| 25 | 2.4 | −2.8 | NA | −2.8 | −0.2 |
| 29 | 4.1 | 2.6 | NA | 2.6 | 3.4 |
| VARIABLE GROUP | | | | | |
| 1 | 1 | 2 | 0.5 | 1.3 | 1.2 |
| 2 | 0.6 | NA | NA | NA | 0.6 |
| 4 | 1.8 | 0 | 1 | 0.5 | 0.9 |
| 5 | 1.9 | 2.5 | NA | 2.5 | 2.2 |
| 7 | 1.6 | −0.1 | NA | −0.1 | 0.8 |
| 8 | 3.2 | 0.4 | −0.4 | 0.0 | 1.1 |
| 10 | 0.9 | 2.1 | 1.7 | 1.9 | 1.6 |
| 11 | 2.5 | 1 | 1.8 | 1.4 | 1.8 |
| 13 | 2.3 | 1.5 | NA | 1.5 | 1.9 |
| 16 | −2.1 | −1.8 | NA | −1.8 | −2.0 |
| 20 | 0.6 | 1.5 | 0 | 0.8 | 0.7 |
| 22 | 3.9 | 1.1 | NA | 1.1 | 2.5 |
| 24 | 5.4 | −0.1 | 0.8 | 0.4 | 2.0 |
| 26 | −0.5 | 1.5 | 0.7 | 1.1 | 0.6 |
| 27 | 4.1 | 4 | 0.4 | 2.2 | 2.8 |
| 28 | 2.5 | 1.6 | NA | 1.6 | 2.1 |
| 30 | NA[1] | NA | NA | NA | NA |

TOTAL AVERAGE K+ 2.18
STANDARD GROUP K+ AVR 3.27
VARIABLE GROUP K+ AVR 1.29
TTEST (not = var) 0.02
TTEST (= var) −0.04
FTEST 0.00
[1]Data not available.
[2]Due to some variation in the actual time at which $T_1$ values were taken, the $T_2$ & $T_3$ average may be considered more reliable than the $T_1$, $T_2$ & $T_3$ average.

Table 3 indicates that the difference between the measured $C_r$ and the expected cardioplegia K+ concentration was reduced in the Variable Group. Table 2 indicates that higher cardioplegia hematocrit, hemoglobin and oxygen content were also demonstrated in the Variable Group. The Variable Group's improved oxygen content, and higher hematocrit and hemoglobin reflect the reduced dilution achieved with the subject method.

From the foregoing, it will be appreciated that numerous variations and modifications may be effected without departing from the spirit and scope of the invention. The appended claims are intended to cover all such modifications and variations.

I claim:

1. A method of obtaining a desired final composition concentration, $C_r$, in an infusion mixture, wherein the infusion mixture is formed by the combination of a flow of a composition crystalloid solution and a flow of a body fluid, said body fluid comprising formed elements that are not substantially permeable to the composition, the method comprising the steps of:

(a) selecting the desired final composition concentration, $C_r$, in the infusion mixture, (b) identifying an empirical equation relating an index of the formed elements in the body fluid and a correction factor, Z, that corrects for the formed element permeability, (c) determining an index value, i, of the formed elements in the flow of body fluid, (d) determining an initial composition concentration in the body fluid, $C_s$, (e) providing one or more of a crystalloid solution composition concentration, $C_k$, a flow rate of body fluid, $Q_b$, and a flow rate of crystalloid solution, $Q_k$, (f) using the identified relationship of step (b) to select a correction factor, $Z_i$, corresponding to the measured index value of step (c), (g) employing $Z_i$, $C_s$ and $C_r$, and provided values of step (e) in one or both of equations (A) and (B):

$$\frac{Q_b}{Q_k} = Z_i * \frac{C_k - C_r}{C_r - C_s} \quad (A)$$

$$C_r = \frac{(Q_b/Z_i * C_s) + (Q_k * C_k)}{Q_b/Z_i + Q_k} \quad (B)$$

to calculate one or more of $C_k$, $Q_b$, $Q_k$ and a ratio of $Q_b:Q_k$.

2. The method of claim 1, wherein step (b) comprises the following steps:

(i) measuring the initial composition concentration, $D_s$, of a body fluid volume, $V_b$, having a known formed element index value, i, (ii) adding a preselected volume of crystalloid solution, $V_k$, of a preselected concentration, $D_k$, to the body fluid, (iii) measuring the resulting composition concentration, $D_r$, of the mixture obtained from step (ii), (iv) repeating steps (i)–(iii) for a plurality of body fluid volumes having the known index to obtain a plurality of resultant concentrations corresponding to the known index, (v) repeating step (iv) for a body fluid volume having an additional known index value, to obtain a plurality of resulting concentrations corresponding to the additional known index value, (vi) optionally repeating step (v) a plurality of times to obtain a plurality of resulting concentrations corresponding to a plurality of known index values, (vii) using each resulting concentration and corresponding $C_s$, $Q_b$ and $Q_k$, to calculate a plurality of correction factors, $Z_i$, according to the formula:

$$Z_i = \frac{V_b}{V_k} * \frac{D_r - D_s}{D_k - D_r} .$$

3. The method of claim 2, further comprising the steps of:
plotting $Z_i$ values against corresponding index values, i, and
deriving the empirical equation relating Z to the index.

4. The method of claim 3, wherein the equation derivation step is effected by a least squares exponential fit of the data.

5. The method of claim 4 wherein the empirical equation is:

$$Z(Hct) = 0.906 * e^{0.00995 * Hct}.$$

6. The method of claim 3, wherein said equation derivation step is effected by a least squares linear fit of the data.

7. The method of claim 1 wherein the body fluid is selected from the group consisting of whole blood, a white blood cell fraction and a platelet fraction.

8. The method of claim 1 wherein the body fluid comprises whole blood.

9. The method of claim 1 wherein the body fluid is whole blood, the composition is a heart-arresting agent, the infusion mixture is cardioplegia, the formed elements are red blood cells, and the index is hematocrit.

10. The method of claim 9 wherein the heart-arresting agent is selected from the group consisting of K+ ion, Mg++ ion, and a combination thereof.

11. A method of obtaining a desired final composition concentration, $C_r$, in an infusion mixture, according to steps (a)–(g) of claim 1, wherein step (e) comprises providing $C_k$, and step (g) comprises selecting a $Q_b:Q_k$ ratio according to the equation:

$$\frac{Q_b}{Q_k} = Z_i * \frac{C_k - C_r}{C_r - C_s} .$$

12. The method of claim 11 wherein the flow rates of the blood and crystalloid solution are controlled by independent pump heads operatively associated with the blood flow and crystalloid solution flow, and wherein said selected ratio of blood flow rate and crystalloid solution flow rate is effected by controlling speeds of the pump heads.

13. The method of claim 11 wherein the flow rates of the blood and the crystalloid solution are controlled by a single pump head operatively associated with both flows, and wherein the selected ratio of blood and crystalloid solution flow rates is effected by controlling inner diameters of tubing conveying the blood and tubing conveying the crystalloid solution.

14. A method for determining the crystalloid solution flow rate, $Q_k$, comprising the steps of:
selecting a $Q_b:Q_k$ ratio according to the method of claim 11,
selecting a desired infusion mixture flow rate, $Q_r$,
calculating the $Q_k$ according to the equation:

$$Q_k = \frac{Q_r}{1 + Q_b/Q_k} .$$

15. A method for determining the body fluid flow rate, $Q_b$, comprising the steps of:
selecting a $Q_b:Q_k$ ratio according to the method of claim 11,
selecting a desired infusion mixture flow rate, $Q_r$,
calculating the $Q_b$ according to the equation:

$$Q_b = \frac{Q_r * Q_b/Q_k}{1 + Q_b/Q_k} .$$

16. A method for determining the crystalloid solution concentration, $C_k$, comprising the steps of:
selecting a $Q_b:Q_k$ ratio according to the method of claim 11,
determining the $C_k$ according to the equation:

$$C_k = C_r + \frac{Q_b}{Q_k} * \frac{(C_r - C_s)}{Z_i} .$$

17. A method of obtaining a desired final composition concentration, $C_r$, in an infusion mixture, wherein the infusion mixture is formed by the combination of a flow of a composition crystalloid solution and a flow of blood, said blood comprising cells that are not substantially permeable to the composition, the method comprising the steps of:

(a) selecting the desired final composition concentration, $C_r$, in the infusion mixture, (b) identifying an empirical equation relating hematocrit to a correction factor, Z, that corrects for the cells' permeability, said empirical equation being accurate over a finite range of $C_k$ values, (c) selecting a $C_k$ that exceeds said finite range, (d) determining the hematocrit of the blood flow, (e) determining an initial composition blood concentration, $C_s$, an initial blood osmolarity, $O_s$, and an osmolarity of the crystalloid solution, $O_k$, (f) providing one or more of the blood flow rate, $Q_b$, crystalloid solution flow rate, $Q_k$, and crystalloid solution composition concentration, $C_k$, (g) using the identified relationship of step (b) to select a correction factor, $Z_i$, corresponding to the measured hematocrit of step (d), (h) employing $Z_i$, $C_s$, $C_r$ and the provided values of step (e) to calculate $Q_b$, $Q_k$, $C_k$, or the $Q_b$:$Q_k$ ratio using an equation:

$$C_r = \frac{(Q_b/Z_i * C_s) + (Q_k * C_k)}{Q_b/Z_i + Q_k + \Delta Q_{rc}}$$

wherein $\Delta Q_{rc}$ is the rate of flow of fluid from inside the cells to outside the cells, and $$\Delta Q_{rc} = Q_{rci} * \left[ 1 - \frac{O_s}{O_r} \right]$$

wherein $Q_{rci}$ is the initial red blood cell intracellular plasma volume, said $Q_{rci}$ being equal to 0.667 times the red cell volume fraction, RCVF, wherein RCVF=1−1/$Z_i$, and wherein $O_r$ is the resulting osmolarity of infusion mixture and is defined by the equation:

$$O_r = \frac{(Q_{rci} + Q_b/Z_i) * O_s + (Q_k * O_k)}{Q_{rci} + Q_b/Z_i + Q_k}$$

18. The method of claim 17 wherein said step of identifying an empirical equation of step (b) comprises the steps of:

(i) measuring the initial composition concentration, $D_s$, of a blood volume, $V_b$, having a known hematocrit value, i, (ii) adding a preselected volume of crystalloid solution, $V_k$, of a preselected concentration, $D_k$, to the body fluid, (iii) measuring the resulting composition concentration, $D_r$, of the mixture obtained from step (ii), (iv) repeating steps (i)–(iii) for a plurality of blood volumes having the known hematocrit value to obtain a plurality of resultant concentrations corresponding to the known hematocrit value, (v) repeating step (iv) for a blood volume having an additional known hematocrit value, to obtain a plurality of resulting concentrations corresponding to the additional known hematocrit value, (vi) optionally repeating step (v) a plurality of times to obtain a plurality of resulting concentrations corresponding to known hematocrit values, (vii) using each resulting concentration and corresponding $D_s$, $V_b$ and $V_k$ to calculate a plurality of correction factors, $Z_i$, according to the formula:

$$Z_i = \frac{V_b}{V_k} * \frac{D_r - D_s}{D_k - D_r}$$

19. The method of claim 18, further comprising the steps of:

plotting $Z_i$ values against corresponding hematocrit values, i, and deriving the empirical equation relating Z to the hematocrit.

20. The method of claim 19 wherein the empirical equation is $$Z_i = 0.906 * e^{0.00995 * Hct}.$$

21. An infusion system for obtaining a desired composition concentration, $C_r$, in an infusion mixture comprising:

a conduit containing a flow of body fluid, and a conduit containing a flow of composition crystalloid solution, said conduits in fluid communication whereby the body fluid and the crystalloid solution are combined to form the infusion mixture, said body fluid comprising formed elements that are not substantially permeable to the composition, means for determining an initial composition concentration, $C_s$, of the flow of body fluid, means for determining a concentration of crystalloid solution, $C_k$, means for determining a formed element index, i, of the body fluid, means for providing either a flow rate of crystalloid solution, $Q_k$, or a flow rate of blood, $Q_b$, a controller that controls body fluid flow rate, $Q_b$, and crystalloid solution flow rate, $Q_k$, to produce the infusion mixture having the desired composition concentration, $C_r$, said controller employing a predetermined equation that relates a correction factor, Z, to the formed element index, so as to select a correction factor, $Z_i$, corresponding to the measured index value, said predetermined equation being accurate over a finite range of $C_k$ values, said controller further employing either or both of equations (A) or (B):

$$\frac{Q_b}{Q_k} = Z_i * \frac{C_r - C_s}{C_k - C_r} \quad (A)$$

$$C_r = \frac{(Q_b/Z_i * C_s) + (Q_k * C_k)}{Q_b/Z_i + Q_k} \quad (B)$$

whereby at least one of $Q_b$, $Q_k$, $C_k$ or the ratio of $Q_b$:$Q_k$ can be calculated.

22. The system of claim 21 wherein the predetermined equation is obtained by a method comprising the steps of:

(i) measuring the initial composition concentration, $D_s$, of a body fluid volume, $V_b$, having a known formed element index value, i, (ii) adding a preselected volume of crystalloid solution, $V_k$, of a preselected concentration, $D_k$, to the blood, (iii) measuring the resulting composition concentration, $D_r$, of the mixture obtained from step (ii), (iv) repeating steps (i)–(iii) for a plurality of body fluid volumes having the known index value to obtain a plurality of resultant concentrations corresponding to the known index value, (v) repeating step (iv) for a body fluid volume having an additional known index value, to obtain a plurality of resulting concentrations corresponding to the additional known index value, (vi) optionally repeating step (v) a plurality of times to obtain a plurality of resulting concentrations corresponding to known index values, (vii) using each resulting concentration, $D_r$, and corresponding $D_s$, $V_b$ and $V_k$, to calculate a plurality of correction factors, $Z_i$, according to the formula:

$$Z_i = \frac{V_b}{V_k} * \frac{D_r - D_s}{D_k - D_r}.$$

23. The system of claim 22, further comprising the steps of:

plotting $Z_i$ values against corresponding index values, i, and deriving the empirical equation relating Z to the index.

24. The system of claim 21 wherein the predetermined equation that relates Z to hematocrit is:

$$Z(Hct) = 0.906 * e^{0.00995 * Hct}.$$

25. An infusion system for obtaining a desired composition concentration, $C_r$, in an infusion mixture comprising:

a conduit containing a flow of body fluid, and a conduit containing a flow of composition crystalloid solution, said conduits in fluid communication whereby the body fluid and the crystalloid solution are combined to form the infusion mixture, said body fluid comprising formed elements that are not substantially permeable to the composition, means for determining an initial composition concentration, $C_s$, of the flow of body fluid, means for determining a concentration of crystalloid solution, $C_k$, means for determining the initial blood osmolarity, $O_s$, means for determining the osmolarity of the crystalloid solution, $O_k$, means for determining a formed element index, i, of the body fluid, means for providing either a flow rate of crystalloid solution, $Q_k$, or a flow rate of blood, $Q_b$, a controller that controls body fluid flow rate, $Q_b$, and crystalloid solution flow rate, $Q_k$, to produce the infusion mixture having the desired composition concentration, $C_r$, said controller employing a predetermined equation that relates a correction factor, Z, to the formed element index, so as to select a correction factor, $Z_i$, corresponding to the measured index value, said predetermined equation being accurate over a finite range of $C_k$ values, said controller further employing either or both of equations (A) or (B):

$$\frac{Q_b}{Q_k} = Z_i * \frac{C_r - C_s}{C_k - C_r} \quad (A)$$

$$C_r = \frac{(Q_b/Z_i * C_s) + (Q_k * C_k)}{Q_b/Z_i + Q_k + \Delta Q_{rc}} \quad (B)$$

whereby at least one of $Q_b$, $Q_k$, $C_k$ or the ratio of $Q_b$:$Q_k$ can be calculated, wherein $\Delta Q_{rc}$ is the rate of flow of fluid from inside the formed elements to outside the formed elements, and $$\Delta Q_{rc} = Q_{rci} * \left[ 1 - \frac{O_s}{O_r} \right]$$

wherein $Q_{rci}$ is the initial red cell intracellular plasma volume, said $Q_{rci}$ being equal to 0.667 times the total red cell volume, RCVF, wherein $RCVF = 1 - 1/Z_i$, and wherein $O_r$ is the resulting osmolarity of the infusion mixture and is defined by the equation:

$$O_r = \frac{(Q_{rci} + Q_b/Z_i) * O_s + (Q_k * O_k)}{Q_{rci} + Q_b/Z_i + Q_k}.$$

26. The system of claim 25 wherein the predetermined equation is obtained by a method comprising the steps of:

(i) measuring the initial composition concentration, $D_s$, of a body fluid volume, $V_b$, having a known formed element index value, i, (ii) adding a preselected volume of crystalloid solution, $V_k$, of a preselected concentration, $D_k$, to the blood, (iii) measuring the resulting composition concentration, $D_r$, of the mixture obtained from step (ii), (iv) repeating steps (i)–(iii) for a plurality of body fluid volumes having the known index value to obtain a plurality of resultant concentrations corresponding to the known index value, (v) repeating step (iv) for a body fluid volume having an additional known index value, to obtain a plurality of resulting concentrations corresponding to the additional known index value, (vi) optionally repeating step (v) a plurality of times to obtain a plurality of resulting concentrations corresponding to known index values, (vii) using each resulting concentration, $D_r$, and corresponding $D_s$, $V_b$ and $V_k$, to calculate a plurality of correction factors, $Z_i$, according to the formula:

$$Z_i = \frac{V_b}{V_k} * \frac{D_r - D_s}{D_k - D_r}.$$

27. The system of claim 26, further comprising the steps of:

plotting $Z_i$ values against corresponding index values, i, and deriving the empirical equation relating Z to the index.

28. The system of claim 25 wherein the predetermined equation that relates Z to hematocrit is:

$$Z(Hct) = 0.906 * e^{0.00995 * Hct}.$$

29. An infusion system for obtaining a desired composition concentration, $C_r$, in an infusion mixture, comprising:

a conduit containing a flow of body fluid, and a conduit containing a flow of composition crystalloid solution, said conduits in fluid communication whereby the body fluid and the crystalloid solution are combined to form the infusion mixture, said body fluid comprising formed elements that are not substantially permeable to the composition, means for determining an initial composition concentration, $C_s$, of the body fluid, means for determining a formed element index, i, of the body fluid, means for providing a ratio of the flow rate of body fluid to the flow rate of crystalloid solution, $Q_b$:$Q_k$, a controller that employs a predetermined equation that relates a correction factor, Z, to the index of the body fluid, so as to select a correction factor, $Z_i$, corresponding to the measured index value, i, said predetermined equation being accurate over a finite range of $C_k$ values, said controller further employing either or both of equations:

$$\frac{Q_b}{Q_k} = Z_i * \frac{C_r - C_s}{C_k - C_r} \quad (A)$$

$$C_r = \frac{(Q_b/Z_i * C_s) + (Q_k * C_k)}{Q_b/Z_i + Q_k} \quad (B)$$

to calculate a crystalloid solution composition concentration, $C_k$, that produces the desired $C_r$.

30. The system of claim 29 wherein the predetermined equation is obtained a method comprising the steps of:

(i) measuring the initial composition concentration, $D_s$, of a blood volume, $V_b$, having a known index value, i, (ii) adding a preselected volume of crystalloid solution, $V_k$, of a preselected concentration, $D_k$, to the blood, (iii) measuring the resulting composition concentration, $D_r$, of the mixture obtained from step (ii), (iv) repeating steps (i)–(iii) for a plurality of blood volumes having the known index value to obtain a plurality of resultant concentrations corresponding to the known index value, (v) repeating step (iv) for a body fluid volume having an additional known index value, to obtain a plurality of resulting concentrations corresponding to the additional known index value, (vi) optionally repeating step (v) a plurality of times to obtain a plurality of resulting concentrations corresponding to known index values, (vii) using each resulting concentration and corresponding $D_s$, $V_b$ and $V_k$, to calculate a plurality of correction factors, $Z_i$, according to the formula:

$$Z_i = \frac{V_b}{V_k} * \frac{D_r - D_s}{D_k - D_r}.$$

31. The system of claim 30, wherein said method further comprising the steps of:

plotting $Z_i$ values against corresponding index values, i, and deriving the empirical equation relating Z to the index.

32. The system of claim 29 wherein the predetermined equation that relates Z to hematocrit is:

$$Z(Hct) = 0.906 * e^{0.00995 * Hct}.$$

33. An infusion system for obtaining a desired composition concentration, $C_r$, in an infusion mixture, comprising:

a conduit containing a flow of body fluid, and a conduit containing a flow of composition crystalloid solution, said conduits in fluid communication whereby the body fluid and the crystalloid solution are combined to form the infusion mixture, said body fluid comprising formed elements that are not substantially permeable to the composition, means for determining an initial composition concentration, $C_s$, of the body fluid, means for determining the initial blood osmolarity, $O_s$, means for determining the osmolarity of the crystalloid solution, $O_k$, means for determining a formed element index, i, of the body fluid, means for providing a ratio of the flow rate of body fluid to the flow rate of crystalloid solution, $Q_b:Q_k$, a controller that employs a predetermined equation that relates a correction factor, Z, to the index of the body fluid, so as to select a correction factor, $Z_i$, corresponding to the measured index value, i, said predetermined equation being accurate over a finite range of $C_k$ values, said controller further employing either or both of equations:

$$\frac{Q_b}{Q_k} = Z_i * \frac{C_r - C_s}{C_k - C_r} \quad (A)$$

$$C_r = \frac{(Q_b/Z_i * C_s) + (Q_k * C_k)}{Q_b/Z_i + Q_k + \Delta Q_{rc}} \quad (B)$$

to calculate a crystalloid solution composition concentration, $C_k$, that produces the desired $C_r$, wherein $\Delta Q_{rc}$ is the rate of flow of fluid from inside the formed elements to outside the formed elements and $$\Delta Q_{rc} = Q_{rci} * \left[ 1 - \frac{O_s}{O_r} \right]$$

wherein $Q_{rci}$ is the initial red blood cell intracellular plasma volume, said $Q_{rci}$ being equal to 0.667 times the red cell volume fraction, RCVF, wherein RCVF=1−1/$Z_i$, and wherein $O_r$ is the resulting osmolarity of infusion mixture and is defined by the equation:

$$O_r = \frac{(Q_{rci} + Q_b/Z_i) * O_s + (Q_k * O_k)}{Q_{rci} + Q_b/Z_i + Q_k}.$$

34. The system of claim 33 wherein the predetermined equation is obtained by a method comprising the steps of:

(i) measuring the initial composition concentration, $D_s$, of a blood volume, $V_b$, having a known index value, i, (ii) adding a preselected volume of crystalloid solution, $V_k$, Of a preselected concentration, $D_k$, to the blood, (iii) measuring the resulting composition concentration, $D_r$, of the mixture obtained from step (ii), (iv) repeating steps (i)–(iii) for a plurality of blood volumes having the known index value to obtain a plurality of resultant concentrations corresponding to the known index value, (v) repeating step (iv) for a body fluid volume having an additional known index value, to obtain a plurality of resulting concentrations corresponding to the additional known index value, (vi) optionally repeating step (v) a plurality of times to obtain a plurality of resulting concentrations corresponding to known index values, (vii) using each resulting concentration and corresponding $D_s$, $V_b$ and $V_k$, to calculate a plurality of correction factors, $Z_i$, according to the formula:

$$Z_i = \frac{V_b}{V_k} * \frac{D_r - D_s}{D_k - D_r}.$$

35. The system of claim 34, wherein said method further comprising the steps of:

plotting $Z_i$ values against corresponding index values, i, and deriving the empirical equation relating Z to the index.

36. The system of claim 33, wherein the predetermined equation that relates Z to hematocrit is:

$$Z(Hct) = 0.906 * e^{0.00995 * Hct}.$$

37. A method for producing a mixture comprising a first fluid having a dissolved substance in a first concentration and a body fluid having a volume of formed elements, said formed elements being not substantially permeable to the dissolved substance, said mixture having a predetermined concentration of the dissolved substance, said method comprising:

establishing a volume of the body fluid;

correcting the volume of the body fluid for the effects of the formed elements that are not substantially permeable to the formed substance;

establishing a volume of the first fluid to achieve the predetermined concentration of the dissolved substance in the mixture; and combining the volume of the first fluid with the corrected volume of the body fluid to form the mixture having the predetermined concentration of the dissolved substance.

38. The method of claim 37, wherein the formed elements respond to the presence of the dissolved substance in the mixture by transferring fluid from within the formed elements to a portion of the mixture outside the formed elements, further comprising:

adjusting the volume of the body fluid for the effect of fluid transferred from the formed elements to the portion of the mixture outside the formed elements.

39. The method of claim 37, wherein the volume of body fluid is flowing and the method takes place throughout the time during which the body fluid volume is flowing.

40. The method of claim 37, wherein the correcting step further comprises:

determining the portion of the body fluid volume that comprises the formed elements.

41. The method of claim 37 wherein the first fluid is crystalloid solution and the dissolved substance is potassium or magnesium ion.

42. An apparatus for producing a mixture comprising a first fluid having a dissolved substance in a first concentration and blood having a volume of formed elements, said formed elements being not substantially permeable to the dissolved substance, said mixture having a predetermined concentration of the dissolved substance, said apparatus comprising:

means for establishing a volume of the blood;

means for correcting the volume of the blood for the effects of the volume and permeability to the dissolved substance of the formed elements;

means for establishing a volume of the first fluid to achieve the predetermined concentration of the dissolved substance in the mixture; and means for combining the volume of the first fluid with the volume of the blood.

43. The apparatus of claim 42, wherein:

the means for correcting the blood volume for the effects of volume and permeability of the formed elements comprises a controller;

the means for establishing the volume of the first fluid comprises a first pump controlled by the controller; and the means for establishing the blood volume comprises a second pump controlled by the controller.

44. The apparatus of claim 43, wherein the means for correcting the blood volume for the effects of volume and permeability of the formed elements further comprises a means for determining the ratio of the volume of formed elements to the total blood volume.

45. The apparatus of claim 42, wherein the first fluid is crystalloid solution and the dissolved substance is magnesium or potassium ion.

46. The method of claim 37, wherein the step of correcting the volume of the body fluid further comprises:

determining an index value of formed elements in the body fluid;

identifying a correction factor based on the index value of formed elements in the body fluid;

applying the correction factor to the volume of body fluid to correct the volume of body fluid for the formed elements that are not substantially permeable to the formed substance.

47. The method of claim 46 wherein the step of applying the correction factor further comprises:

applying the following formula to relate the predetermined dissolved substance concentration to the volume of body fluid:

$$\frac{Q_b}{Q_k} = Z * \frac{(C_k - C_r)}{(C_r - C_s)}$$

wherein $C_r$ is the predetermined dissolved substance concentration of the mixture, $Q_b$ is the volume of body fluid, $Q_k$ is the volume of first fluid, Z is the correction factor, $C_s$ is the initial dissolved substance concentration of the body fluid, and $C_k$ is the concentration of the dissolved substance in the first fluid.

48. The method of claim 37 wherein the body fluid comprises whole blood.

49. The method of claim 37 wherein the body fluid is whole blood, the first fluid is a heart-arresting agent, the mixture is cardioplegia solution, the formed elements are red blood cells, and the index is hematocrit.

* * * * *